(12) United States Patent
Ducharme

(10) Patent No.: US 12,420,059 B2
(45) Date of Patent: Sep. 23, 2025

(54) PRESSURE-SENSING GUIDEWIRE

(71) Applicant: Ampullae, Inc., Buffalo, NY (US)

(72) Inventor: Richard Ducharme, Buffalo, NY (US)

(73) Assignee: Ampullae, Inc., Buffalo, NY (US)

( * ) Notice: Subject to any disclaimer, the term of this patent is extended or adjusted under 35 U.S.C. 154(b) by 951 days.

(21) Appl. No.: 17/510,257

(22) Filed: Oct. 25, 2021

(65) Prior Publication Data

US 2022/0126061 A1    Apr. 28, 2022

Related U.S. Application Data

(60) Provisional application No. 63/123,095, filed on Dec. 9, 2020, provisional application No. 63/105,015, filed on Oct. 23, 2020.

(51) Int. Cl.
*A61M 25/00* (2006.01)
*A61M 25/01* (2006.01)
*A61M 25/09* (2006.01)

(52) U.S. Cl.
CPC .... *A61M 25/0067* (2013.01); *A61M 25/0102* (2013.01); *A61M 2025/0002* (2013.01); *A61M 2025/0042* (2013.01); *A61M 2025/09183* (2013.01); *A61M 2205/0266* (2013.01); *A61M 2205/0294* (2013.01); *A61M 2205/3331* (2013.01); *A61M 2205/581* (2013.01); *A61M 2205/582* (2013.01); *A61M 2205/583* (2013.01)

(58) Field of Classification Search
CPC .......... A61M 25/0067; A61M 25/0102; A61M 2025/0042; A61M 2025/09183; A61M 2205/0266; A61M 2205/0294; A61M 2205/3331; A61M 2205/581; A61M 2205/582; A61M 2205/583; A61M 2025/0002
See application file for complete search history.

(56) References Cited

U.S. PATENT DOCUMENTS

| | | | | |
|---|---|---|---|---|
| 5,865,801 A | * | 2/1999 | Houser | A61B 5/036 607/101 |
| 2009/0125007 A1 | | 5/2009 | Splinter | |
| 2014/0081244 A1 | * | 3/2014 | Voeller | A61B 5/0215 604/528 |
| 2014/0191221 A1 | * | 7/2014 | Benwadih | G01L 9/008 257/40 |

FOREIGN PATENT DOCUMENTS

WO    2014168737 A1    10/2014

OTHER PUBLICATIONS

"PCT Search Report and Written Opinion, PCT/US2021/56516", Jan. 31, 2022, 36 pages.

* cited by examiner

*Primary Examiner* — Eric F Winakur
*Assistant Examiner* — Hy Khanh Doan
(74) *Attorney, Agent, or Firm* — Edward C. Kwok; VLP Law Group LLP

(57) ABSTRACT

An endovascular device may include (a) a proximal end, configured for communicating a pressure signal to a receiver; (b) a distal end comprising a pressure sensor that is based on (i) a piezoelectric polymer layer; and (ii) first and second electrodes, electrically insulated from each other, each contacting the piezoelectric polymer layer, wherein the pressure sensor derives the pressure signal from the first and second electrodes; and (c) a device body, which provides one or more conductors to carry the pressure signal from the distal end to the proximal end.

21 Claims, 1 Drawing Sheet

PRESSURE-SENSING GUIDEWIRE

CROSS REFERENCE TO RELATED APPLICATIONS

The present application relates to and claims priority of (i) U.S. provisional application ("Provisional Application I"), Ser. No. 63/105,015, entitled "Pressure-Sensing Guidewire," filed on Oct. 23, 2020, and (ii) U.S. provisional application ("Provisional Application II"), Ser. No. 63/123,095, entitled "Pressure-Sensing Guidewire," filed on Dec. 9, 2020. The disclosures of the Provisional Applications I and II are hereby incorporated by reference in their entireties.

BACKGROUND OF THE INVENTION

1. Field of the Invention

The present invention relates to medical devices. In particular, the present invention relates to an endovascular device (e.g., a guidewire or a catheter) that provides tactile feedback to an operator as the device traverses the vasculature of a patient.

2. Discussion of the Related Art

Endovascular devices, such as guidewires and catheters, are used in treatment of many different vascular diseases. In that context, a guidewire is a flexible wire that provides a rail along which a larger, stiffer catheter may safely follow to reach the target vasculature. A typical endovascular device is about 100 cm long and is designed to travel from the patient's groin to a target that may be as far up as the brain, navigating through the tortuous anatomy along the way. During use, whether diagnostic or therapeutic (e.g. stenting), a physician relies on their fine-tuned sense of feel, while guided by a simultaneously captured two-dimensional x-ray image, to safely navigate the endovascular device to the target site of the procedure. In this regard, the physician's judgement is based neither entirely on their vision nor their tactile sense, but a complex interpretation of the device's motion relative to expectation—a skill developed from significant practice and experience, but by no means perfect.

Procedures involving endovascular devices present many risks, including incidental perforation of a blood vessel by either the guidewire or the catheter. This risk is also substantially increased when the procedure is performed by a less-experienced physician whose skill is not yet fully developed. It is often a physician's nightmare that, while having put a patient at risk in the presence of medical fellows in training, the physician suddenly loses their sense of feel about how the device is functioning.

Many suppliers have recently developed endovascular robotic systems that drive and control catheters and guidewires and that perform therapeutic activities (e.g. Corindus, available from Hansen Medical). These robotic systems have many benefits, such as removing the physician from close proximity with an x-ray source to the safety of a cockpit which provides the physician electronic control of device movements at a very fine resolution. Furthermore, there are many medical emergency procedures that require a physician of a highly specialized skill on a moment's notice, and yet are not frequently performed at many smaller facilities to warrant having such a skilled physician on-staff. A prime example is the endovascular treatment of stroke (i.e., thrombectomy). Coupled with the fact that these cases are unscheduled and frequently occur in the middle of the night, it would be advantageous for a physician to be able to drive the robot remotely either from home for a patient in a rural hospital, or cover for a colleague in another time zone, when a case arises in the middle of the night.

A major hurdle to wide deployment of such robotic systems is the inadequate tactile feedback that is provided to the physician to allow them to assess in real time the pressure the endovascular device is applying to the vasculature. In the prior art, an endovascular device (e.g., a catheter) may at best provide a tube along its length to allow measurement of a fluid pressure at the distal end of the catheter. For that reason, the adoption rates of such robotic systems have been low, as physicians feel that they are flying by vision only, without their critical feel for device performance.

Thus, there is a need for a method or device that provides tactile measurements that could be used by a highly skilled physician for diagnosis, aid in the training of new fellows, and enable robotic control of catheters and guidewires.

SUMMARY

According to one embodiment of the present invention, an endovascular device may include (a) a proximal end, configured for communicating a pressure signal to a receiver; (b) a distal end comprising a pressure sensor that is based on (i) a piezoelectric polymer layer; and (ii) first and second electrodes, electrically insulated from each other, each contacting the piezoelectric polymer layer, wherein the pressure sensor derives the pressure signal from a signal detected in the first and second electrodes; and (c) a device body, which provides one or more conductors for carrying the pressure signal from the distal end to the proximal end. In some embodiments, the receiver interprets the pressure signal and provides a user a representation of the pressure signal audially, visually, or through a response over a haptic interface.

In some embodiments, the conductors at the device body (i) may run parallel along substantially the entire length of a core wire; (ii) may include an insulated coiled wire wrapped around substantially the entire length of a core wire; (iii) may include parallel coiled conducting wires; (iv) may include parallel wires that run along and around a core wire; (v) may include conductive ink applied on an electrically insulated core wire; or (vi) may include conductors that pass through a hollow Nitinol hypotube, which electrically insulates a stylet, except at the distal end.

In one embodiment, the piezoelectric polymer layer in the pressure sensor may include one or more piezoelectric or ferroelectric copolymers, such as a copolymer of vinylidene difluoride (VDF) and trifluroethylene (TrFB). The piezoelectric polymer layer may be 5.0-50.0 um thick, preferably 10.0-30.0 um thick, even more preferably about 20 um thick.

According to one embodiment of the present invention, the pressure sensor may be formed from a core wire coated by the piezoelectric polymer layer. The core wire may include a tip having a linear or stepwise tapered end, so as to enhance flexibility. In one embodiment, the piezoelectric polymer layer is coated onto the tapered end of the core wire by a dip-coating process or by direct application. The core wire may also be encased in an electrically insulated hypotube (e.g., Nitinol hypotube). In that embodiment, the tapered end is exposed outside of the hypotube. The pressure sensor may further include a coil wrapping around the piezoelectric polymer layer.

The present invention is better understood upon consideration of the detailed description below, in conjunction with the drawings.

DETAILED DESCRIPTION OF THE PREFERRED EMBODIMENTS

The present invention provides an integrated pressure sensor at the distal end of an endovascular device, such as a guidewire or a catheter. The integrated pressure sensor may be configured for transmitting a signal ("pressure signal") to the proximal end of the endovascular device that represents a pressure or an acceleration, or both. The pressure sensor may include, for example, one or more piezoelectric or ferroelectric copolymers, such as the copolymers of vinylidene difluoride (VDF) and trifluroethylene (TrFE) (e.g., P(VDF-TrFE)). P(VDF-TrFE) may be obtained from Piezotech, a subsidiary of Arkema SA. In this detailed description, the present invention is illustrated by a guidewire. One of ordinary skill in the art would recognize that the present invention is also applicable to other endovascular devices, such as catheters.

Figure 1:
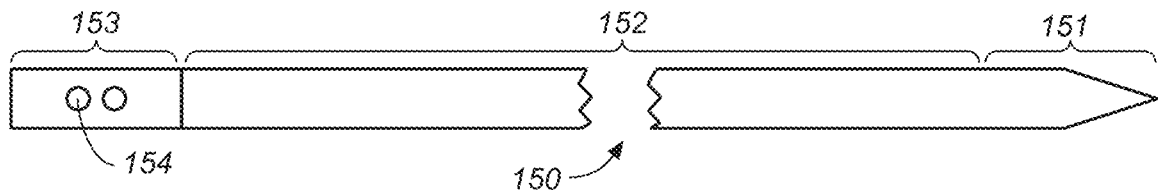
FIG. 1 shows exemplary endovascular device 150 (e.g., a guide wire), having proximal end 153, device body 152 and distal end 151.

According to one embodiment of the present invention, FIG. 1 shows exemplary endovascular device 150, having proximal end 153, device body 152 and distal end 151. An example of endovascular device 150 is a guidewire, which may include:

(a) proximal end 153, which provides connection 154 to a receiver that (i) receives one or more specific electrical signals; (ii) amplifies the received signals, when desired; (iii) interprets the received signals; and (iv) notifies a user of each of the received signals audially, visually, or through a response over a haptic interface, individually or in any combination of these modalities; (The receiver may be part of a pitch-catch electronic drive system that causes detection of the electrical signals.)

(b) distal end 151, at which a sensor (e.g., a pressure sensor) that is based on a piezoelectric polymer is located; and (c) guidewire body 152, which may be of conventional guidewire construction and materials[1], providing one or more conductors in the form of:

[1] e.g., a guidewire with (i) a core including a nitinol wire and a Teflon, polyurethane or Pebax jacket); and (ii) an outer layer coated with a thin hydrophilic coating for improved lubricity during passage through the vasculature.

(i) one or more conductors running parallel along the entire length of a core wire;

(ii) an insulated coiled wire wrapped around the entire length of a core wire;

(iii) parallel coiled conducting wires;

(iv) parallel wires that run along and around a core wire;

(v) conductive ink applied on an electrically insulated core wire; or (vi) that pass through a hollow Nitinol hypotube, within which a core wire forms a stylet that is electrically insulated by the Nitinol hypotube until the distal end, where the conductors are electrically connected to the integrated pressure sensor.

The sensor may include a piezoelectric polymer (e.g., P(VDF-TrFE) layer that is approximately 20 um thick, provided between first and second electrodes that is configured to transfer an electrical signal (e.g., a voltage difference between the first and second electrodes).

Figure 2:
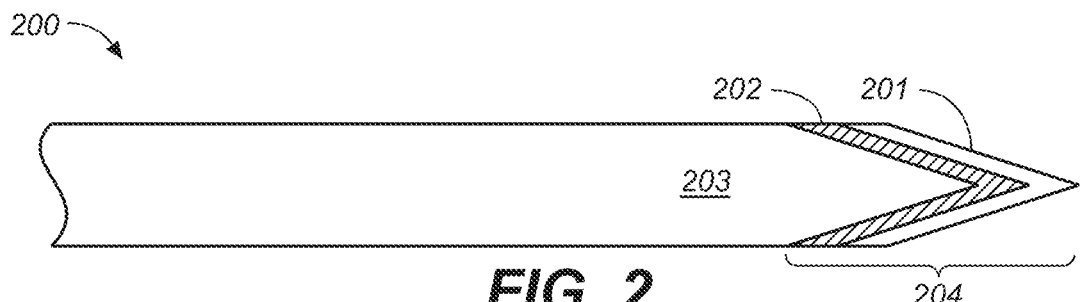
FIG. 2 shows pressure sensor 200 provided in the form of a coated distal wire according to one embodiment of the present invention.

According to one embodiment of the present invention, FIG. 2 shows pressure sensor 200 provided in the form of a coated distal wire. As shown in FIG. 2, core wire 203 (i.e., a grounded nitinol guidewire) is provided a linear or stepwise tapered end 204. The diminished diameter of core wire 203 increases flexibility at tapered end 204 of core wire 203. Over tapered end 204 may be formed piezoelectric polymer layer 202 (e.g., a 20-um thick layer) using, for example, a dip-coating process or by direct application. Conductive electrode 201, which is electrically connected to the proximate end (not shown) through one of the configurations of the guidewire body described above, for example, is provided over and contacts piezoelectric polymer layer 202. Core wire 203 and pressure sensor 200 may be coated with a polymer jacket for electrical insulation and lubricity.

In some embodiments, core wire 203 need not be tapered.

Figure 3:
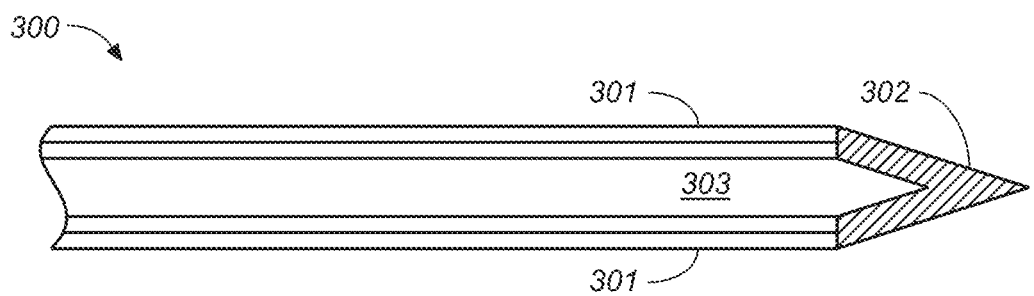
FIG. 3 shows pressure sensor 300 provided at the distal end of a guidewire that is constructed as a hypotube, according to one embodiment of the present invention.

According to one embodiment of the present invention, FIG. 3 shows pressure sensor 300, provided at the distal end of a guidewire that is encased in a hypotube. As shown in FIG. 3, core wire 303 (e.g., a nitinol core wire) is provided as an electrically insulated inner core of hypotube 301. Hypotube 301 provides an insulation surrounding core wire 303, except at the distal end of core wire 301, where a tapered end of core wire 303 is exposed. Like pressure sensor 200 of FIG. 2, core wire 303 may be linearly or stepwise tapered. Pressure sensor 300 is formed by encapsulating the tapered end in piezoelectric polymer layer 302 (e.g., a 20-um thick layer), which may be formed using, for example, a dip-coating process or by direct application. In this configuration, core wire 303 serves as a return electrode. Conceptually, as an electrical device, pressure sensor 300 mimics a headphone jack.

Figure 4:
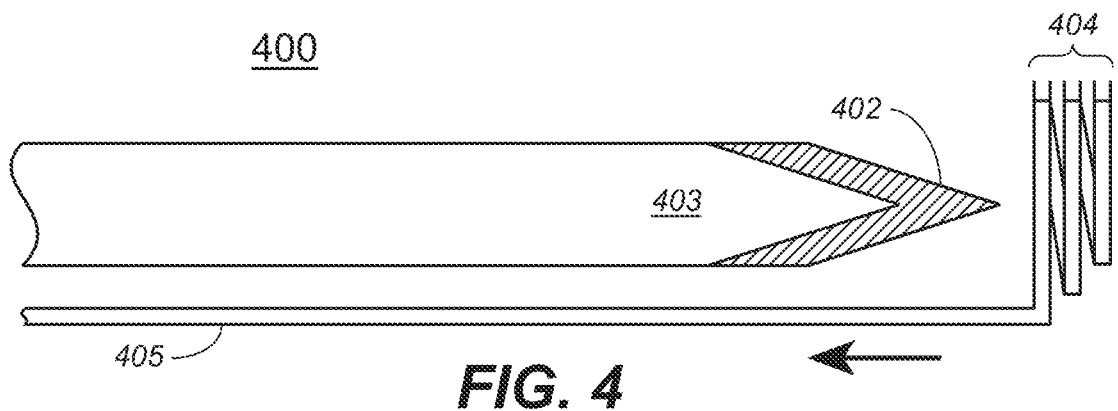
FIG. 4 shows pressure sensor 400 provided at the distal end of a guidewire with coil 404 wrapping around piezoelectric polymer layer 402 and serving as a return signal path, according to one embodiment of the present invention.

According to one embodiment of the present invention, FIG. 4 shows pressure sensor 400 provided at the distal end of a guidewire with coil 404 wrapping around piezoelectric polymer layer 402 and serving as a return signal path. In FIG. 4, Like pressure sensor 200 of FIG. 2 or pressure sensor 300 of FIG. 3, core wire 403 is linearly or stepwise tapered. Pressure sensor 400 is formed by encapsulating the tapered end of core wire 403 in piezoelectric polymer layer 402 (e.g., a 20-um thick layer), which may be formed using, for example, a dip-coating process or by direct application. Coil 404 wraps around piezoelectric polymer layer 402. (In FIG. 4, for clarity, coil 404 is shown "slid out" of piezoelectric polymer layer 402; in this implementation, coil 404 is tightly wound over piezoelectric polymer layer 402.) Coil 404 is connected by wire 405 to the proximal end of the guidewire (not shown). In this embodiment, both coil 404 and wire 405 are electrically insulated from core wire 403 along the entire length of core wire 403, serving as return electrode to the active or opposite electrode of core wire 403. The guidewire, including core wire 403, coil 404 and wire 405, may be encapsulated in a non-conductive polymer jacket.

The above detailed description is provided merely to illustrate specific embodiments of the present invention and is not intended to be limiting. Many variations and modifications within the scope of the present invention are possible. The present invention set forth in the accompanying claims.

I claim:

1. An endovascular device, comprising:
   (a) a proximal end, configured for communicating a pressure signal to a receiver;
   (b) a distal end comprising a pressure sensor that is based on (i) a piezoelectric polymer layer encapsulating an exposed tip of a core wire, the exposed tip being located at the distal end; and (ii) first and second electrodes, electrically insulated from each other, each contacting the piezoelectric polymer layer, wherein the pressure sensor derives the pressure signal from the first and second electrodes; and
   (c) a device body, which provides one or more conductors for carrying the pressure signal from the distal end to the proximal end.

2. The endovascular device of claim 1, wherein the conductors running parallel along substantially the entire length of the core wire.

3. The endovascular device of claim 1, wherein the conductors comprise an insulated coiled wire wrapped around substantially the entire length of the core wire.

4. The endovascular device of claim 1, wherein the conductors comprise parallel coiled conducting wires.

5. The endovascular device of claim 1, wherein the conductors comprise parallel wires that run along and around the core wire.

6. The endovascular device of claim 1, wherein the conductors comprise conductive ink applied on an electrically insulated core wire.

7. The endovascular device of claim 1, wherein the conductors pass through a hollow Nitinol hypotube.

8. The endovascular device of claim 7, further comprising a stylet that is electrically insulated by the nitinol hypotube until the distal end.

9. The endovascular device of claim 1, wherein the receiver interprets the pressure signal and provides a user a representation of the pressure signal audially, visually, or through a response over a haptic interface.

10. The endovascular device of claim 1, wherein the endovascular device is one of: a guidewire and a catheter.

11. The endovascular device of claim 1, the piezoelectric polymer layer comprises one or more piezoelectric and ferroelectric copolymers.

12. The endovascular device of claim 11, wherein the piezoelectric polymer layer comprises a copolymer of vinylidene difluoride (VDF) and trifluroethylene (TrFE).

13. The endovascular device of claim 1, wherein the piezoelectric polymer layer is 5-50 um thick.

14. The endovascular device of claim 13, wherein the piezoelectric polymer layer is between 10.0-30.0 um thick.

15. The endovascular device of claim 1, wherein the exposed tip has a linear or stepwise tapered end.

16. The endovascular device of claim 1, wherein the piezoelectric polymer layer is coated onto the core wire by a dip-coating process or by direct application.

17. The endovascular device of claim 1, wherein the core wire is encased in the electrically insulated hypotube.

18. The endovascular device of claim 17, wherein the hypotube comprises nitinol.

19. The endovascular device of claim 18, wherein the core wire includes a tip having a linear or stepwise tapered end which is not electrically insulated by the hypotube.

20. The endovascular device of claim 1, wherein the pressure sensor further comprises a coil wrapping around the piezoelectric polymer layer.

21. The endovascular device of claim 1, wherein one of the first and second electrodes is provided by the exposed portion of the core wire.

* * * * *